United States Patent [19]

Prahl

[11] Patent Number: 5,617,651
[45] Date of Patent: Apr. 8, 1997

[54] FOREFOOT RELIEVING SHOE, MORE PARTICULARLY FOR POSTOPERATIVE TREATMENT

[75] Inventor: Jan Prahl, Rullstorf, Germany

[73] Assignee: Heil- und Hilfsmittel Vertriebs GmbH, Scharnebeck, Germany

[21] Appl. No.: 441,758

[22] Filed: May 16, 1995

[30] Foreign Application Priority Data

Apr. 25, 1995 [DE] Germany .................. 295 06 925.2

[51] Int. Cl.⁶ ............................. A43B 7/00; A43B 21/30
[52] U.S. Cl. ............................. 36/110; 36/7.8; 36/27
[58] Field of Search ...................... 36/81, 27, 28, 36/7.8, 106, 110, 38

[56] References Cited

U.S. PATENT DOCUMENTS

| | | | |
|---|---|---|---|
| 2,394,281 | 2/1946 | Williams | 36/38 |
| 2,421,019 | 5/1947 | Doherty | 36/38 |
| 2,508,318 | 5/1950 | Wallach | 36/38 |
| 4,546,557 | 10/1985 | Barouk et al. | 36/110 |
| 4,561,195 | 12/1985 | Onoda et al. | 36/28 |
| 4,726,127 | 2/1988 | Barouk | 36/110 |
| 4,881,329 | 11/1989 | Crowley | 36/27 |
| 5,138,776 | 8/1992 | Levin | 36/38 |
| 5,185,943 | 2/1993 | Tong et al. | 36/27 |

FOREIGN PATENT DOCUMENTS 1280676  2/1962  France ......................... 36/7.8

Primary Examiner—Marie D. Patterson
Attorney, Agent, or Firm—Friedrich Kueffner

[57] ABSTRACT

For ensuring longer wear or utilization times without damage to the walking block, the sole portion (11) of the forefoot relieving shoe, more particularly for the postoperative treatment, with a different sole portion elasticity and with a sole portion (11) which is substantially triangular in a side view or in a vertical longitudinal cross-section and possessing a thickness which diminishes toward the rear and which terminates before the metatarsal region of the wearer, of a homogeneous foamed plastic (19), wherein a spring (20, 21) is embedded which can be tensioned against the pressure exerted by a foot on the shoe.

8 Claims, 3 Drawing Sheets

FOREFOOT RELIEVING SHOE, MORE PARTICULARLY FOR POSTOPERATIVE TREATMENT

The present invention relates to a forefoot relieving shoe, more particularly for postoperative treatment, with a sole portion which is essentially triangular in a side view or in a vertical longitudinal section and possessing a thickness which diminishes toward the rear and which terminates before the metatarsal region of the wearer.

BACKGROUND OF THE INVENTION

A forefoot relieving shoe of this type is known from the U.S. Pat. No. 4,546,557. Surgical interventions within the forefoot region, especially in hallux valgus operations, call for a postoperative period during which the forefoot (which cannot as yet be subjected to any strain) has to be treated with care. If the patient does not wish to walk with the aid of crutches during this period, then the relieving shoe mentioned in the beginning can provide a solution, whose obliquely disposed foot bedding, in connection with the sole portion terminating before the metatarsal region, ensures that the patient is able to put the weight on the foot and also to safely roll on the same. The shoe according to said U.S. patent specification has a compressible sole possessing a compressibility which increases from the rear to the front. This design is intended to serve for a better absorption of shocks within the front area of the shoe. Apart from the circumstance that the adjustment of a differing degree of compressibility in one sole portion is technically difficult and/or costly, plastic sole portions, when in use, are subjected to considerable mechanical stresses which, in the event of material fatigue, may easily lead to large plastic portions breaking off, after which the sole portion is unserviceable. A reinforcement of this sole portion which is possible in principle, is opposed by the requirement for as low as possible a weight, just like the requirements calling for the desired elasticity of the sole portion when rolling the foot.

That is why the technical problem of the present invention is to develop further the shoe to the effect that, without damage being caused to the walking block, it makes longer wearing periods or periods of use possible and ensures a good wear comfort, particularly with respect to the desired differing elasticity of the sole portion.

The technical problem is resolved by the forefoot relieving shoe possessing the features listed in the claim 1.

SUMMARY OF THE INVENTION

According to the invention, the sole portion is comprised of a foamed plastic, in which a spring is embedded and which can be tensioned against the pressure exerted on the shoe by a foot. This spring thus brings about a permanently elastic reinforcement, in which, by the adjustment of the spring constants in each sole portion (segment), the desired elastic recovery properties to different extents are just as realizable as with the aid of the spring, the synthetic foamed material employed, which may be any plastics, improves in a corresponding manner the durability of the sole portion. It is possible to realize the invention with only a single spring or with a group of springs which are embedded in the foamed plastic independently of each other or in an interconnected fashion.

By preference, the spring extends essentially over the entire length of the sole (with the exception of marginal areas).

According to a further construction of the invention, the forefoot relieving shoe is provided with a sole portion possessing a compressibility which increases from the rear toward the front, which enhances the rolling comfort.

In a special embodiment of the invention, a leaf spring is embedded on the top side of the sole which preferably terminates flush with the marginal areas of the sole top side. In this way a smooth bearing surface results which is readily laid on and attached to the relief shoe bedding sole and in which the spring is able to transmit its effect close to the foot bedding sole. Contrary to the state of the art, the differing elasticity is not ensured by the homogeneous sole portion plastic member, but by the spring.

According to a further improvement, on the underside of the leaf spring, the flat sections of a curved spring bent aside at the end bear against said leaf spring or they are connected to the same. The combination of a superjacent leaf spring with a curved spring permits an adaptation of the spring configuration to the sole portion geometry in the form of a reinforcement which is substantially extensible across the entire sole portion member.

As is known in principle according to the state of the art, the one-piece sole portion possesses a supporting carrier plate projecting over the, in the longitudinal cross-section, triangular sole portion, on which the sole portion front area extends in an S-configured manner as far as to the bottom area of the sole portion. In this case the leaf spring extends into the area of the supporting carrier plate.

According to a further construction of the invention, the curved spring possesses a first anterior leg which extends, relative to the lower sole portion front area following the supporting carrier plate, approximately parallel and/or vertical to the sole portion surface area. The second leg of the curved spring extends preferably relative to the sole portion surface at an acute angle which, by preference, is between 35° and 55°. Between the two legs, a substantially circular center piece is located in such a way that, in cross-section, the curved spring comes to possess the approximate configuration of an obliquely disposed V-section with different inclinations of the two legs. By preference, the front bent-aside flat section of the curved spring, within the transitional region from the supporting carrier plate to the triangular sole portion and/or the rear bent-aside flat section, shortly before the calcaneal tuberosity of the foot, is disposed so as to bear against the leaf spring.

In order to ensure that the spring is unable to become displaced in the plastic member, the leaf spring and/or the curved spring possess at least one perforation which is reached through by the foamed plastics. In the flat section springs, the perforations may be produced in the form of drilled holes. Subsequent to the spring having been aligned in an injection molding device, the sole portion plastic material is cast into the injection mold, if necessary, under pressure where, while including the perforations, it flows through the free injection molding cavities and, after curing, bears against the spring to its full extent while penetrating the perforations and is able to cure. By preference, the perforations are longitudinally oval in cross-section. According to another construction of the invention, the point before the contact area with the curved spring presents itself as the location for the perforation and, in the curved spring, the posterior leg which is constructed so as to be longer than the anterior leg.

It is preferred that the spring is comprised of an elastomeric plastic which possesses a greater hardness than the foamed plastic of the sole portion.

BRIEF DESCRIPTION OF THE DRAWINGS

In the drawings, an embodiment example of the invention is depicted. Thus

DETAILED DESCRIPTION OF THE PREFERRED EMBODIMENT

Figure 1:
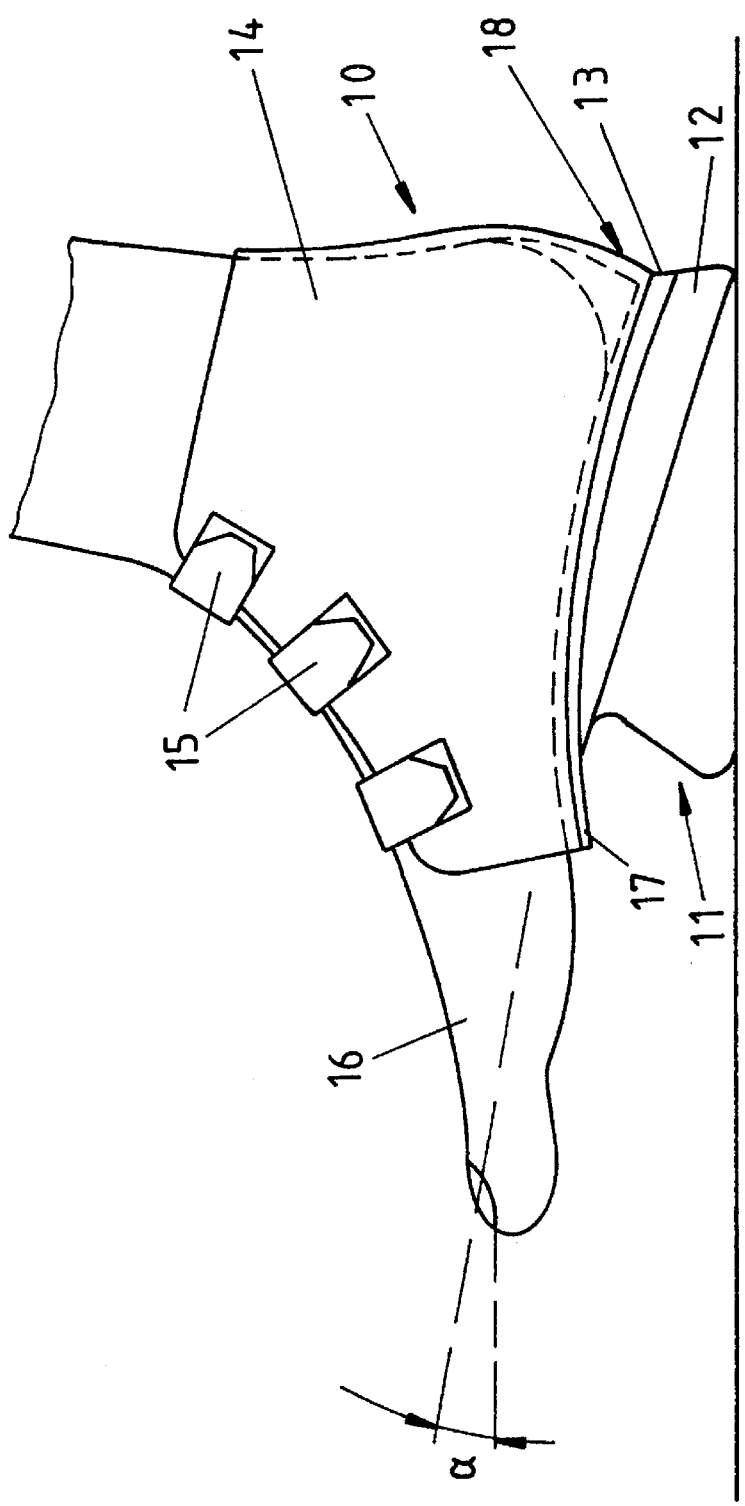
FIG. 1 shows a schematic side view of a forefoot relieving shoe.

The forefoot relieving shoe 10 is comprised of a sole portion 11, possibly an intermediate portion or top member 12, which may form part of the foot bedding 13, as well as of a portion comprising two shells 14 connected to the top member or the foot bedding which, by way of example, can be closed by means of Velcro strip fasteners 15. The shells 14 may be comprised of leather, plastic or textile fabric. The forefoot relieving shoes is configured in such a way that the forefoot 16 is exposed and raised in the direction of the point of the foot, which is brought about by the substantially triangular contour of the sole portion 11. The angle of inclination α is regularly between 5° and 15°. The foot bedding 13 terminates in the metatarsal region which must not be subjected to any load. When walking, the wearer of the forefoot relieving shoe 10 is able to first of all put down the shoe in the region of the heel 18, to roll on the foot in the forward direction without running the risk of touching the ground with the forefoot or toes.

Figure 2:
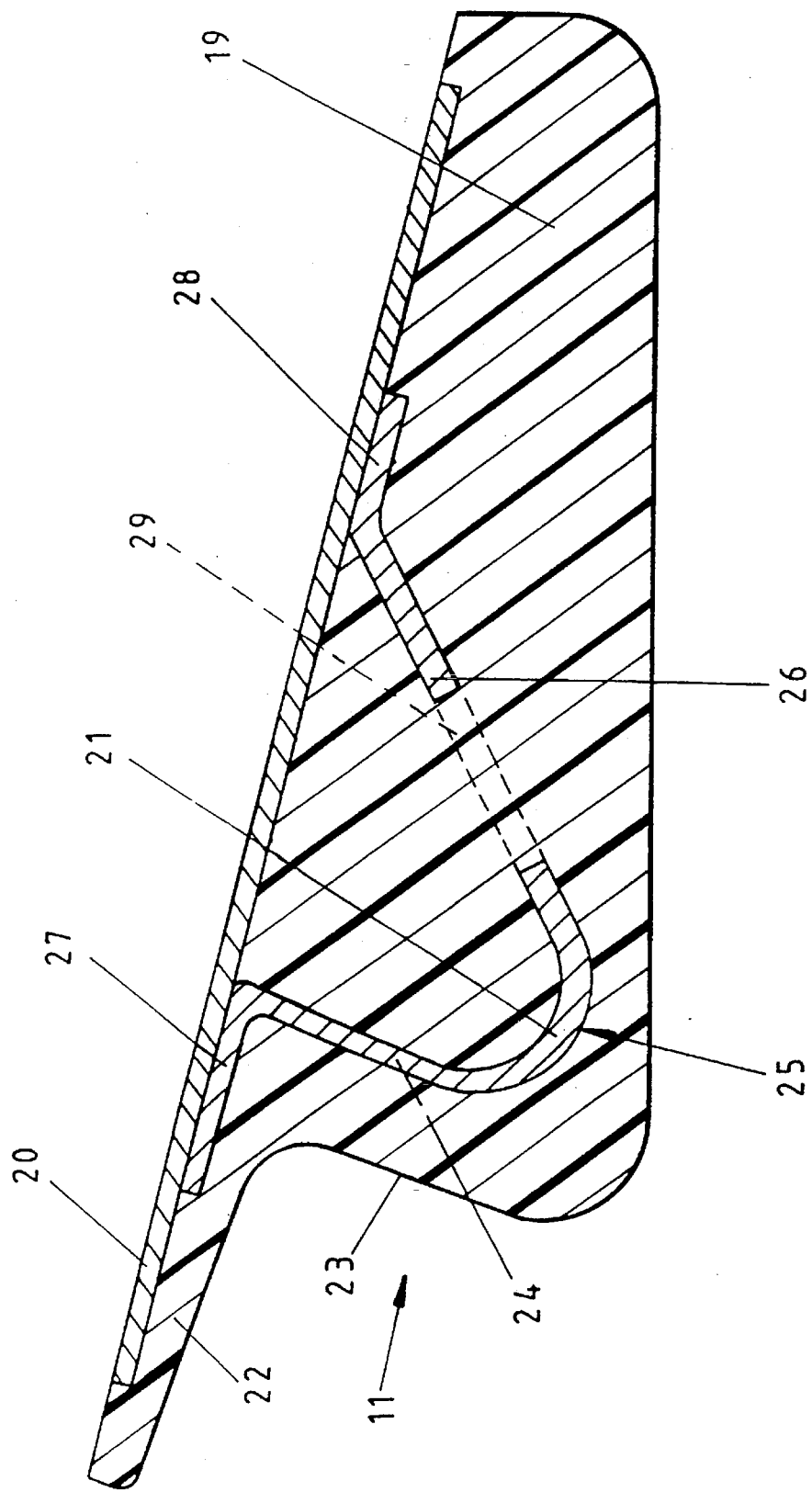
FIG. 2 shows a longitudinal cross-section through a sole portion.
Figure 3:
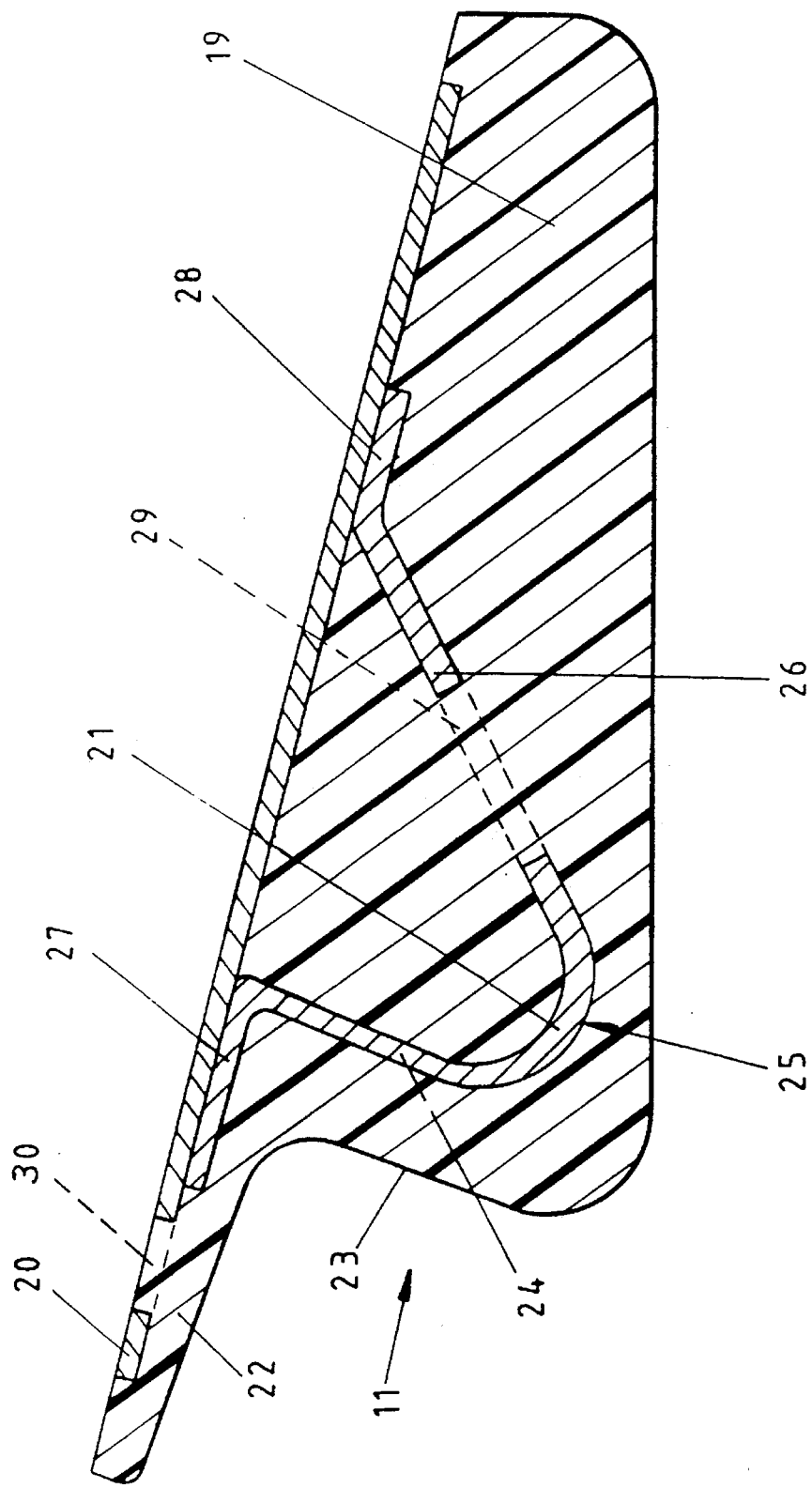
FIG. 3 shows another embodiment of the sole portion.

As is shown by the longitudinal cross-sectional view of the sole portion 11 in FIG. 2, the same is constructed in the form of a one-piece homogeneous foamed plastic component in which a spring is embedded and which is comprised of two parts, viz. a leaf spring 20 and a curved spring 21. The leaf spring 20, with the exception of a lateral marginal area, extends to its full extent over the entire length and width of the sole portion 11, more particularly it extends as far as into the area of an anterior supporting carrier plate 22 which projects above the triangular sole portion which, incidentally, is followed by the front wall 23 in the form of an S-shaped bend. The leaf spring 20 may be provided with a perforation 30 which is located before the contact area with the curved spring 21, as shown in FIG. 3. The curved spring 21 is comprised of an anterior leg 24, a curved base portion 25 and of a posterior leg 26. At the end, bend-aside flat sections 27 and 28 follow the anterior and posterior legs, which bear to their full extent against the underside of the leaf spring 20. The front flat section is located approximately in the area of the extension of the front wall, that is to say within the area of transition between the supporting carrier plate 22 and the substantially triangular sole portion body 19.

The anterior leg is spacedly disposed approximately parallel to the front face or front wall 23 of the sole portion and vertical to the leaf spring 20, whereas the rear leg 26 runs out at an acute angle to the leaf spring 20. In addition, the rear leg 26 is provided with a longitudinally oval perforation 29, which is reached through by the foamed material of the sole portion 19. The leaf spring 20 may be provided with corresponding perforations, preferably within the area of the front supporting carrier plate 22 and/or within the rear area, i.e. behind the flat section 28 which is bent aside at the end.

The forefoot relieving shoe with the sole portion specified in greater detail in FIG. 2 has, in comparison with the embodiments known from the state of the art, been optimized. A homogeneous rubber substance which is simple to prepare from a production engineering viewpoint can be selected as the material for the sole portion, which is strengthened by the reinforcement with the aid of the spring 20, 21 so that this rubber substance will be able to withstand the walking stresses over a longer period of time. By means of the spring 20, 21, a load distribution is achieved which compensates the wearing compression of the foamed material (rubber). Hereby it will not be possible from the very outset for overloads to occur in the event of strong compressions. The spring 20, 21 is configured in such a way that it covers the entire load surface area of the top side and is equipped with a semi-circular stiffening 24, 25 reaching into the front rolling area. The bent-aside flat sections 27 and 28 may be secured to the underside of the leaf spring 20 by bonding. The double-layer spring 20, 21 increases the forefoot flexibility and supports the rolling motion in such a way that, in the direction toward the heel, a further thread for absorbing the shocks is obtained. In the rolling edge, by means of the springs 20, 21, an increased pressure is applied, whereby the forefoot is relieved in a freely suspended manner.

As material, a plastic may be chosen which is mechanically stable independently of temperature, i.e. which, in frost, is just as resistant to fracture as under extreme heat influences of up to 40° C. If necessary, the spring 20, 21 is pretreated with the aid of adhesion intensifiers in such a way that it enters into an intensive intercrescence with the foamed material 19. It is also possible for carbon fibers to be employed as fabrication material for the spring 20, 21.

What is claimed is:

1. A forefoot relieving shoe for a foot having a metatarsal region and a calcaneal tuberosity, the forefoot relieving shoe having a longitudinal direction and a front and a rear, the forefoot relieving shoe comprising a single-piece sole portion having an essentially triangular cross-section in the longitudinal direction, the sole portion having an upper side, wherein a thickness of the triangular sole portion decreases toward the rear, and wherein the sole portion ends before the metatarsal region, the sole portion comprising a homogeneous foamed plastic body, a supporting carrier plate projecting toward the front from the triangular sole portion, a leaf spring embedded in the sole portion so as to be flush with marginal areas of the upper side of the sole portion, the leaf spring having a bottom side, further comprising a curved spring having an anterior leg and a posterior leg, and a front flat section connected to the anterior leg and a rear flat section connected to the posterior leg, wherein the front and rear flat sections of the curved spring are attached to the bottom side of the leaf spring, the anterior leg extending essentially parallel to a sole portion front face located adjacent the supporting carrier plate and perpendicular to the upper side of the sole portion, and the posterior leg extending at an angle of between 35° and 55° relative to the upper side of the sole portion, wherein the front flat section of the curved spring is located in a transition area between the support carrier plate and the triangular sole portion, and the rear flat section is located a short distance in front of the calcaneal tuberosity.

2. The forefoot relieving shoe according to claim 1, wherein the leaf spring extends essentially over an entire length of a sole of the shoe.

3. The forefront relieving shoe according to claim 1, wherein the triangular sole portion has a compressibility which increases from the rear toward the front.

4. The forefoot relieving shoe according to claim 1, wherein the curved spring is of a flat material having at least one perforation, the foamed plastic body extending through the perforation.

5. The forefoot relieving shoe according to claim 4, wherein the perforation has a longitudinally oval cross-section.

6. The forefoot relieving shoe according to claim 1, wherein the leaf spring has a perforation located in front of the front flat section of the curved spring.

7. The forefoot relieving shoe according to claim 1, wherein the posterior leg of the curved spring has a perforation.

8. The forefoot relieving shoe according to claim 1, wherein the leaf spring and curved spring are comprised of an elastomeric plastic.

* * * * *